(12) United States Patent
Polonka

(10) Patent No.: US 8,470,802 B2
(45) Date of Patent: *Jun. 25, 2013

(54) SENSORY MODIFIER

(75) Inventor: Jack Polonka, Peekskill, NY (US)

(73) Assignee: Conopco, Inc., Englewood Cliffs, NJ (US)

( * ) Notice: Subject to any disclaimer, the term of this patent is extended or adjusted under 35 U.S.C. 154(b) by 435 days.

This patent is subject to a terminal disclaimer.

(21) Appl. No.: 12/247,478

(22) Filed: Oct. 8, 2008

(65) Prior Publication Data

US 2010/0087389 A1    Apr. 8, 2010

(51) Int. Cl.
*A61K 37/715* (2006.01)
*A61K 37/718* (2006.01)

(52) U.S. Cl.
USPC ............. 514/54; 514/60; 536/102; 536/123.1

(58) Field of Classification Search
USPC ............................ 514/54, 60; 536/102, 123.1
See application file for complete search history.

(56) References Cited

U.S. PATENT DOCUMENTS

| | | | |
|---|---|---|---|
| 3,890,300 A | 6/1975 | Huchette et al. | |
| 6,248,338 B1 | 6/2001 | Cardinali et al. | |
| 6,331,291 B1 | 12/2001 | Glace et al. | |
| 6,348,090 B1 | 2/2002 | Grillo et al. | |
| 6,706,288 B2 * | 3/2004 | Gustavsson et al. | 424/497 |
| 6,822,091 B1 | 11/2004 | Kesselmans et al. | |
| 7,192,598 B2 | 3/2007 | Aronson et al. | |
| 7,247,294 B1 | 7/2007 | Shore et al. | |
| 7,250,158 B1 | 7/2007 | Shore et al. | |
| 7,361,363 B2 | 4/2008 | Barrow et al. | |
| 2002/0006386 A1 | 1/2002 | Ibsen et al. | |
| 2003/0152540 A1 | 8/2003 | Putman et al. | |
| 2004/0234486 A1 | 11/2004 | Hashimoto | |
| 2005/0002888 A1 | 1/2005 | Bleckmann et al. | |
| 2005/0208009 A1 | 9/2005 | Bonnardel et al. | |
| 2006/0034876 A1 | 2/2006 | Barrow et al. | |
| 2006/0134045 A1 | 6/2006 | Cao et al. | |
| 2007/0237730 A1 | 10/2007 | Polonka et al. | |
| 2008/0063619 A1 | 3/2008 | Olsen et al. | |

FOREIGN PATENT DOCUMENTS

| | | |
|---|---|---|
| DE | 196 27 498 A1 | 1/1998 |
| EP | 1 051 967 | 11/2000 |
| EP | 1 230 914 | 8/2002 |
| EP | 1 923 044 | 5/2008 |
| WO | 97/28790 | 8/1997 |
| WO | 02/39950 | 5/2002 |
| WO | 2005/107695 | 11/2005 |
| WO | WO 2005107695 A1 * | 11/2005 |
| WO | 2008/002890 | 3/2008 |

OTHER PUBLICATIONS

PCT International Search Report and Witten Opinion on Application No. PCT/EP2009/061523 dated Feb. 26, 2010.
Chang et al., "*Interactive plasticizing-antiplasticizing effects of water and glycerol on the tensile properties of tapioca starch films*"; Food Hydrocolloids, vol. 20, No. 1, 2006, pp. 108.
Myllarinen et al., "*Effect of glycerol on behaviour of amoylose and amylopectin films*". Carbohydrate Polymers, Applied Science Publishers, Ltd., vol. 50, No. 4. 2002, pp. 388-361.
PCT International Search Report and Written Opinion on Application No. PCT/EP2009/061625 dated Feb. 26, 2010.
Patent Abstracts of Japan for Publication No. 2006-111549 and abstract.
Patent Abstracts of Japan for Publication No. 2005-232049 and abstract.
Patent Abstracts of Japan for Publication No. 2005-232271 and abstract.
Derwent Abstract for JP 2003-095908.
Co-pending application for: Applicant: Polonka; U.S. Appl. No. 12/247,488, filed Oct. 8, 2008, entitled: Universal Sensory Structurant.

* cited by examiner

*Primary Examiner* — Shaojia Anna Jiang
*Assistant Examiner* — Michael C Henry
(74) *Attorney, Agent, or Firm* — Edward A. Squillante, Jr.

(57) ABSTRACT

Sensory modifiers and compositions comprising sensory modifiers are described. The sensory modifiers comprise polysaccharide carbohydrate having at least about 75% by weight amylopectin and the polysaccharide carbohydrate has been treated and swollen with a substantially anhydrous solvent.

16 Claims, No Drawings

SENSORY MODIFIER

FIELD OF THE INVENTION

The present invention is directed to sensory modifiers and a method for making the same. More particularly, the present invention is directed to sensory modifiers comprising a polysaccharide carbohydrate comprising at least about 75% by weight amylopectin wherein the carbohydrate has been treated and swollen with a substantially anhydrous solvent. The sensory modifiers of this invention can be used in formulating topical compositions which unexpectedly result in superior sensory benefits after application.

BACKGROUND OF THE INVENTION

Many consumers are concerned with the characteristics of their skin. For example, consumers are concerned with the degree of pigmentation of their skin, freckles and/or age spots. Other consumers are concerned with skin imperfections that include wrinkles, large pores, acne and/or an oily appearance.

While it is desirable for consumers to hide or mask skin imperfections with topical compositions, such compositions tend to leave the consumer with poor sensory sensations. For example, conventional skin lightening compositions formulated with silicone elastomers can be tacky and oily, thereby yielding an unpleasant feel during the skin lightening process.

There is an increasing interest to develop topical compositions that deliver a benefit to the consumer yet do not result in undesirable sensory sensations upon application. This invention, therefore, is directed to sensory modifiers comprising a polysaccharide carbohydrate comprising at least about 75% by weight amylopectin wherein the carbohydrate has been treated and swollen with a substantially anhydrous solvent. The sensory modifiers of this invention can be used in formulating topical compositions which unexpectedly result in superior sensory benefits after application.

ADDITIONAL INFORMATION

Efforts have been disclosed for making topical compositions that provide skin benefits. In U.S. Patent Application No. 2007/0237730 A1, cosmetic compositions with soft focus properties are described.

Other efforts have been disclosed for making topical compositions that provide skin benefits. In U.S. Pat. Nos. 7,247,294 and 7,250,158, skin lightening agents and compositions are described.

Still other efforts have been disclosed for making topical compositions that provide skin benefits. In U.S. Pat. No. 7,192,598, wet-skin treatment compositions are described.

None of the additional information above describes a sensory modifier comprising a polysaccharide carbohydrate comprising at least about 75% by weight amylopectin wherein the carbohydrate has been treated and swollen with a substantially anhydrous solvent. Moreover, none of the additional information above describes a topical composition comprising a sensory modifier as described herein.

SUMMARY OF THE INVENTION

In a first aspect, the present invention is directed to a sensory modifier comprising a polysaccharide carbohydrate comprising at least about 75% by weight amylopectin wherein the carbohydrate has been treated and swollen with a substantially anhydrous solvent.

In a second aspect, the present invention is directed to a method for making the sensory modifier of the first aspect of this invention, the method comprising the steps of:
 (a) contacting a polysaccharide carbohydrate comprising at least about 75% by weight amylopectin with a substantially anhydrous solvent to produce a mixture; and
 (b) heating the mixture to produce the sensory modifier.

In a third aspect, the present invention is directed to a topical composition comprising the sensory modifier of the first aspect of this invention.

All other aspects of the present invention will more readily become apparent upon considering the detailed description and examples which follow.

Topical composition, as used herein, is meant to mean a composition suitable for application onto skin of humans and free of gellation. Skin, as used herein, includes the skin on the face, neck, chest, back, arms, axilla, hands, legs and scalp. Treated, as used herein, means coming into contact with in order to induce swelling. Swollen, as used herein, means at least about doubling in size. Substantially anhydrous solvent means a solvent having less that about 6 percent by weight water, and preferably, having from about 0.001 to about 5 percent by weight water, and most preferably, having from about 0.001 to less than about 2% by weight water. Comprising, as used herein, is meant to include consisting essentially of and consisting of. Comprising at least about 75% by weight amylopectin means at least 75% by weight amylopectin based on total weight of the polysaccharide carbohydrate. Free of gellation or no gellation means showing no endothermic gellation peak when analyzing, with a differential scanning calorimeter (DSC Q2000 from TA Instruments), mixtures of sensory modifier and water (50/50 and 30/70 by weight, respectively) heated at 1° C./minute and scanned from 25 to 82° C.

The topical composition of the present invention can be in the form of a liquid, lotion, cream, serum, gel, soap bar or toner, or applied via a face mask, or patch. The topical composition of the present invention is preferably one that at the very least lightens skin, moisturizes skin and/or provides anti-aging benefits to the skin, where anti-aging benefits are meant to include reducing the effect of sunlight on the skin. All ranges identified herein are meant to implicitly include all ranges subsumed therein if for example, reference to the same is not explicitly made.

DETAILED DESCRIPTION OF THE PREFERRED EMBODIMENTS

There is generally no limitation with respect to the polysaccharide carbohydrate comprising at least about 75% by weight amylopectin that may be used in this invention other than that the same is suitable for use in topical compositions. Preferred polysaccharide carbohydrate suitable for use in this invention comprises from about 78 to about 100%, and most preferably, from about 80 to about 100% by weight amylopectin, based on total weight of the polysaccharide carbohydrate and including all ranges subsumed therein. Typically, such polysaccharide carbohydrate has an initial (unswollen) average particle diameter from about 1 to about 15 microns, and preferably, from about 2 to about 12 microns, and most preferably, from about 5 to about 9 microns, including all ranges subsumed therein. Moreover, such a polysaccharide carbohydrate typically comprises from about 0.5 to about 16%, and preferably, from about 2 to about 13%, and most preferably, from about 4 to about 10% by weight water, based on total weight of the polysaccharide carbohydrate and including all ranges subsumed therein. The often desired polysaccharide carbohydrate comprising at least about 75% by weight amylopectin that may be used in this invention is waxy corn starch, tapioca or a mixture thereof whereby the waxy corn starch and tapioca are commercially available from suppliers like National Starch and Chemical Company as well as Millennium Food Tech Co., Ltd.

The anhydrous solvent suitable for use in this invention typically has a polar component from about 7 to about 15, and preferably, from about 8 to about 12; a hydrogen bonding component from about 14 to about 20, and preferably, from about 15 to about 19, and a dispersion component from about 12 to about 19, and preferably, from about 13 to about 18, including all ranges subsumed therein and as determined by the Hansen parameter component system where:

$$\partial_t^2 = \partial_d^2 + \partial_p^2 + \partial_h^2, \text{ and}$$

$\partial_t^2$=total Hildebrand parameter;
$\partial_d^2$=dispersion component;
$\partial_p^2$=polar component; and
$\partial_h^2$=hydrogen bonding component.

In a preferred embodiment, the anhydrous solvent comprises at least one of dipropylene glycol (DPG), polyethylene glycol (PEG) and diglycerine (DG). In a most preferred embodiment, the anhydrous solvent comprises a mixture of dipropylene glycol, polyethylene glycol (especially, PEG-4) and diglycerine whereby the mixture preferably comprises from about 30 to about 50%, and most preferably, from about 35 to about 45% by weight dipropylene glycol based on total weight of the anhydrous solvent and including all ranges subsumed therein. In yet another preferred embodiment, the weight ratio of polyethylene glycol to diglycerine is 30:70 to 70:30 and most preferably, 45:55 to 55:45, including all ratios subsumed therein.

When making the sensory modifier of the present invention, polysaccharide carbohydrate and anhydrous solvent are combined at a weight ratio from about 1:4 to about 4:1, and preferably, from about 1:3 to about 3:1, and most preferably, from about 2:3 to about 3:2. The combined polysaccharide carbohydrate and anhydrous solvent mixture is typically heated to a temperature from about 55 to about 90° C., and preferably, from about 65 to about 85° C., and most preferably, from about 70 to about 80° C. The combined polysaccharide carbohydrate and anhydrous solvent mixture is typically heated for about 0.5 to about 6 hours, and preferably, from about 1 to about 5 hours, and most preferably, from about 1.5 to about 4.5 hours.

The resulting sensory modifier (i.e., swollen polysaccharide carbohydrate structurant) typically has polysaccharide carbohydrate with a final average particle diameter that is from about 1.5 to about 6, and preferably, from about 2 to about 5, and most preferably, from about 2.5 to about 3.5 times greater than the initial average particle diameter of the polysaccharide carbohydrate. In an especially preferred embodiment, the polysaccharide carbohydrate is functionally modified (i.e., surface modified) with a $C_{10}$-$C_{16}$ alkyl and/or alkenyl, and preferably, a $C_{12}$-$C_{14}$ alkyl and/or alkenyl. Typically from about 0.01 to about 6, and preferably, from about 0.03 to about 4, and most preferably, from about 0.1 to about 3% by weight of the polysaccharide carbohydrate is functionalized, based on total weight of the polysaccharide carbohydrate. When preparing the topical composition of this invention, typically the same comprises from about 0.02 to about 15%, and preferably, from about 0.1 to about 10%, and most preferably, from about 0.3 to about 8% by weight of the sensory modifier. Moreover, and in another preferred embodiment, the topical composition of this invention is substantially free of (i.e., <2% by weight of the composition) silicone elastomers. In a most preferred embodiment, the topical compositions of this invention comprise from about 0.0 to less than about 0.5% by weight silicone elastomer.

It should be known that commercially acceptable and conventional vehicles may be used, acting as diluents, dispersants and/or carriers for the topical composition described herein. Therefore, the cosmetically acceptable vehicle suitable for use in this invention may be aqueous-based, anhydrous or an emulsion whereby a water-in-oil or oil-in-water emulsion is generally preferred. If the use of water is desired, water typically makes up the balance of the topical composition, and often, makes up from about 5 to about 99%, and most preferably, from over 50 to about 90% by weight of the topical composition, including all ranges subsumed therein.

In addition to water, organic solvents may be optionally included to act as carriers or to assist carriers within the compositions of the present invention. Illustrative and non-limiting examples of the types of organic solvents suitable for use in the present invention include alkanols like ethyl and isopropyl alcohol, mixtures thereof or the like.

Other optional additives suitable for use include ester oils like isopropyl myristate, cetyl myristate, 2-octyldodecyl myristate, avocado oil, almond oil, olive oil, neopentylglycol dicaprate, mixtures thereof or the like. Typically, such ester oils assist in emulsifying the topical composition of this invention, and an effective amount is often used to yield a stable, and most preferably, water-in-oil emulsion.

Emollients may also be used, if desired, as carriers within the topical composition of the present invention. Alcohols like 1-hexadecanol (i.e., cetyl alcohol) are often desired as are the emollients generally classified as silicone oils and synthetic esters. Silicone oils, while not required, can be used and they include cyclic or linear polydimethylsiloxanes containing from 3 to 9, preferably from 4 to 5, silicon atoms. Non-volatile silicone oils useful as an emollient material in the topical composition described herein include polyalkyl siloxanes, polyalkylaryl siloxanes and polyether siloxane copolymers.

The ester emollients that may optionally be used are:
(1) alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.
(2) ether-esters such as fatty acid esters of ethoxylated fatty alcohols.
(3) polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
(4) wax esters such as beeswax, spermaceti, stearyl stearate and arachidyl behenate.
(5) sterol esters, of which cholesterol fatty acid esters are examples.

Emollients, when used, typically make up from about 0.1 to about 50% by weight of the topical composition, including all ranges subsumed therein.

Fatty acids having from 10 to 30 carbon atoms may also be included as cosmetically acceptable carriers within the composition of the present invention. Illustrative examples of such fatty acids include pelargonic, lauric, myristic, palmitic, stearic, isostearic, oleic, linoleic, arachidic, behenic or erucic acid, and mixtures thereof. Compounds that are believed to enhance skin penetration, like dimethyl sulfoxide, may also be used as an optional carrier.

Humectants of the polyhydric alcohol type may also be employed in the topical composition of this invention. The humectant often aids in increasing the effectiveness of the emollient and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycerol or sodium hyaluronate. The amount of humectant may range anywhere from 0.2 to 25%, and preferably, from about 0.5 to about 15% by weight of the topical composition, based on total weight of the composition and including all ranges subsumed therein.

Thickeners may also be utilized as part of the cosmetically acceptable carrier in the topical composition of the present invention. Typical thickeners include cross-linked acrylates (e.g. Carbopol 982), hydrophobically-modified acrylates (e.g. Carbopol 1382), taurate copolymers like acrylamide/sodium acryloyldimethyltaurate copolymer, ammonium acryloyldimethyltaurate/VP copolymer (e.g., Simulgel® made available by Seppic, Aristoflex® AVC made available by Clariant), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0 to 5%, usually from 0.001 to 5%, optimally from 0.01 to 2% by weight of the total weight of the topical composition. In an often preferred embodiment, taurate copolymers are used in the topical compositions of this invention.

Collectively, the water, solvents, silicones, esters, fatty acids, humectants and/or thickeners will constitute the cosmetically acceptable carrier in amounts from 1 to 99.9%, preferably from 80 to 99% by weight.

Surfactants may also be present in topical composition of the present invention. Total concentration of the surfactant will range from about 0 to about 40%, and preferably, from about 0 to about 20%, optimally from about 0 to about 5% by weight of the composition. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; mono- and di-fatty acid esters of ethylene glycol; fatty acid monoglyceride; sorbitan, mono- and di-$C_8$-$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants, when used, include soap, alkyl ether sulfate and sulfonates, alkyl sulfates and sulfonates, alkylbenzene sulfonates, alkyl and dialkyl sulfosuccinates, $C_8$-$C_{20}$ acyl isethionates, acyl glutamates, $C_8$-$C_{20}$ alkyl ether phosphates and combinations thereof.

Perfumes may be used in the composition of this invention. Illustrative non-limiting examples of the types of perfumes that may be used include those described in Bauer, K., et al., *Common Fragrance and Flavor Materials*, VCH Publishers (1990).

Illustrative yet non-limiting examples of the types of fragrances that may be used in this invention include myrcene, dihydromyrenol, citral, tagetone, cis-geranic acid or citronellic acid, mixtures thereof or the like.

Preferably, the amount of fragrance employed in the topical composition of this invention is in the range from about 0.0% to about 10%, more preferably, about 0.00001% to about 5 wt %, most preferably, about 0.0001% to about 2%.

Various types of active ingredients may be used in the topical compositions of the present invention. Actives are defined as skin benefit agents other than emollients and other than ingredients that merely improve the physical characteristics of the composition. Although not limited to this category, general examples include talcs and silicas, as well as alpha-hydroxy acids, beta-hydroxy acids, peroxides, zinc salts, and sunscreens.

Beta-hydroxy acids include salicylic acid, for example. Zinc pyrithione is an example of the zinc salts useful in the topical composition of the present invention.

Sunscreens include those materials commonly employed to block ultraviolet light. Illustrative compounds are the derivatives of PABA, cinnamate and salicylate. For example, avobenzophenone (Parsol 1789®), octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the compositions can vary depending upon the degree of protection desired from the sun's UV radiation. Additives that reflect or scatter the suns rays may also be employed. These additives include oxides like zinc oxide and titanium dioxide.

Many topical compositions, especially those containing water, should be protected against the growth of potentially harmful microorganisms. Anti-microbial compounds, such as triclosan, and preservatives are, therefore, typically necessary. Suitable preservatives include alkyl esters of p-hydroxybenzoic acid, hydantoin derivatives, propionate salts, and a variety of quaternary ammonium compounds. Particularly preferred preservatives of this invention are methyl paraben, propyl paraben, phenoxyethanol and benzyl alcohol. Preservatives will usually be employed in amounts ranging from about 0.1% to 2% by weight of the composition.

Still other ingredients that may be used with the topical composition of this invention include dioic acids (e.g., malonic acid, sebacic acid), antioxidants like vitamin E, other vitamins, like vitamin C and its derivatives, recorcinols and its derivatives (including those esterified with, for example, ferulic acid, vanillic acid or the like) and retinoids, including retinoic acid, retinal, retinol and retinyl esters, conjugated linoleic acid, petroselinic acid, plant extracts including Kudzu and Chamomile extracts, and mixtures thereof, as well as any other conventional ingredients well known for wrinkle-reducing, skin whitening (especially, niacinamide), anti-acne effects and reducing the impact of sebum.

When making topical composition of the present invention, the desired ingredients, including the sensory modifier, are mixed, in no particular order, and usually at temperatures from about ambient to about 80° C. and under atmospheric pressure.

The packaging for the composition of this invention can be a patch, bottle, tube, roll-ball applicator, propellant driven aerosol device, squeeze container or lidded jar.

The examples which follow are provided to illustrate and facilitate an understanding of the invention. The examples are not intended to limit the scope of the claims.

EXAMPLE 1

Anhydrous solvent was mixed with corn starch (about 71% amylopectin), waxy corn starch (about 100% amylopectin) and Tapioca (about 83% amylopectin). Each of the mixtures was made with one part by weight solvent to one part by weight polysaccharide carbohydrate. The mixtures were heated to 70° C. for three hours. The resulting sensory modifiers were combined with 70% water (30% sensory modifier) and heated to 70° C. for one hour. The water content of 70% was chosen such that the same is consistent with water content in an end use, topical composition.

| Solvent | Polysaccharide Carbohydrate | Results/stability after addition to H₂O (70%) |
|---|---|---|
| DPG | Corn starch | Fail - gellation |
| PEG-4 | Corn starch | Fail - gellation |
| DPG | Waxy corn starch | Pass - no gellation |
| PEG-4 | Waxy corn starch | Pass - no gellation |
| DPG | Tapioca | Pass - no gellation |
| PEG-4 | Tapioca | Pass - no gellation |

The results indicate that polysaccharide carbohydrate consistent with this invention (e.g., waxy corn starch and tapioca) results in a sensory modifier that yields no gellation in a 70% water formulation.

EXAMPLE 2

Anhydrous solvent having varied Hanson Parameters were used to make sensory modifiers. Anhydrous solvent (one part by weight) and polysaccharide carbohydrate comprising at least about 75% by weight amylopectin (one part by weight) were combined and heated to 70° C. for three hours. The resulting sensory modifiers were added to water (70% water and 30% sensory modifier) and heated to 70° C. for one hour. The water content of 70% was chosen such that the same is consistent with water content in an end use, topical composition.

| Solvent | Tapioca Size Increase (swelling) | Waxy corn starch size increase (swelling) | Results/stability after addition to H₂O | Hanson Parameters | | |
|---|---|---|---|---|---|---|
| | | | | H-bonding | Polarity | Dispersion |
| Glycerin | 150% | 200% | Fail, gellation | 29.3 | 12.1 | 17.4 |
| Propylene glycol | 115% | 170% | Fail, gellation | 23.3 | 9.4 | 16.8 |
| PEG-4 | 115% | 170% | Pass, no gellation | 17.3 | 10.0 | 17.3 |
| DPG | 100% | 130% | Pass, no gellation | 17.7 | 10.6 | 16.5 |
| PEG-2 | 125% | 190% | Fail, gellation | 21.0 | 12.0 | 16.6 |
| PEG-6 | 100% | 140% | Pass, no gellation | 15.6 | 9.1 | 17.1 |
| Butylene glycol | 100% | 140% | Fail, gellation | 21.7 | 9.0 | 16.4 |
| 5% H₂O/95% DPG | 100% | 130% | Pass, no gellation | 18.9 | 10.9 | 16.3 |
| 10H₂O/90 DPG | 100% | 130% | Fail, gellation | 20.9 | 11.2 | 16.1 |
| 70% DPG/30% glycerine | 125% | 170% | Fail, gellation | 21.2 | 11.1 | 16.8 |
| 35% DPG/35% PEG-4/30% glycerine | 145% | 190% | Pass, no gellation | 20.0 | 11.0 | 16.9 |
| 25% DPG/25% PEG-4/50% glycerine | 150% | 200% | Fail, gellation | 23.4 | 11.6 | 16.9 |
| 70% DPG/30% DG | 125% | 160% | Pass, no gellation | 18.8 | 11.0 | 17.5 |
| 40% DPG/30%/ PEG-4/30% DG | 140% | 190% | Pass, no gellation | 18.7 | 11.0 | 17.6 |
| 50% DPG/50% DG | 125% | 170% | Pass, no gellation | 19.4 | 11.4 | 18.0 |

The results indicate that anhydrous solvent selected according to this invention results in a sensory modifier that yields no gellation in a 70% water formulation, as assessed with a differential scanning calorimeter via the procedure described herein.

EXAMPLES 3-31

Commercially available moisturizers, such as Dove® Pro-Age® Beauty Body Lotion were modified and assessed as described below. Waxy corn starch and tapioca deplete of alkyl and/or alkenyl functionalization did swell as well as polysaccharide carbohydrate with functionalization. Skilled panelists assessed all modified compositions. Sensory modifiers were prepared by heating to 70° C. for three hours.

A. Compositions made in Examples 3-5 were prepared with 0.5, 1 and 2% by weight tapioca, respectively added to commercially available moisturizers. As tapioca increased, negative sensory (draggy, non-silky) attributes were realized.

B. Compositions made in Examples 6-8 were prepared with 0.5, 1 and 2% by weight sensory modifier, respectively, made according to this invention (50% tapioca, 50% aqueous solvent made with 40% DPG, 30% PEG-4, 30% DG). As sensory modifier was increased, the composition became more silky with excellent sensory benefits.

C. Compositions made in Examples 9-11 were prepared in a manner similar to the one used to make the compositions of examples 6-8 except that $C_{12}$ alkyl functionalized (2%) tapioca was used. Assessment revealed exceptional sensory performance, increasing with the addition of sensory modifier.

D. Compositions made in examples 12-14 were prepared in a manner similar to the one described for examples 9-11 except that functionalized waxy corn starch was used. Assessment revealed exceptional sensory performance, increasing with the addition of sensory modifier.

E. Compositions made in Examples 15-17 were prepared in a manner similar to the one used to make the compositions in Examples 3-5 except that 1% by weight of a taurate copolymer (e.g., Simulgel) was also added. No improvement to sensory attributes were realized.

F. Compositions made in Examples 18-20 were prepared in a manner similar to the one used to make the composition in Examples 6-8 except that 1% by weight taurate copolymer (e.g., Simulgel) was used. Sensory benefits of the compositions were even better than the benefits realized for the compositions of those of Examples 6-8.

G. Compositions of Examples 21-23 and 24-26 were made in a manner similar to the one used to make the compositions of Examples 9-11 and 12-14, except that 1% by weight taurate copolymer (Simulgel) was also used. Assessment revealed exceptional sensory benefits.

H. Compositions of Examples 27-30 were prepared with 0.5% potato starch, 0.5% swollen potato starch (treated as described for tapioca in Examples 6-8), 0.5% potato starch and 1% taurate copolymer, and 0.5% swollen potato starch and 1% by weight taurate copolymer, respectively. All compositions were draggy and had poor sensory attributes.

The results indicate that sensory modifiers prepared according to this invention yield compositions with very desirable sensory benefits and especially when a functionalized polysaccharide carbohydrate is used with a taurate copolymer.

What is claimed:

1. A sensory modifier comprising a polysaccharide carbohydrate comprising at least about 75% by weight amylopectin wherein the polysaccharide carbohydrate has been treated and swollen with a substantially anhydrous solvent and further wherein the polysaccharide carbohydrate and anhydrous solvent are at a weight ratio from about 1:4 to about 4:1 and heated from about 55 to about 90° C. for about 0.5 to about 6 hours after being combined and the sensory modifier with treated and swollen polysaccharide carbohydrate is free of gellation and further wherein the polysaccharide carbohydrate is functionally modified with a $C_{10}$-$C_{16}$ alkyl and/or alkenyl, and from about 0.01 to about 6 percent by weight of the polysaccharide is functionalized.

2. The sensory modifier according to claim 1 wherein the polysaccharide carbohydrate comprises from about 78 to about 100% by weight amylopectin, an average initial particle diameter from about 1 to about 15 microns and an average swollen particle diameter that is from 1.5 to about 6 times greater than the initial particle diameter.

3. The sensory modifier according to claim 1 wherein the substantially anhydrous solvent has a polar component from about 7 to about 15, a hydrogen bonding component from about 14 to 20, and a dispersion component from about 12 to about 19.

4. The sensory modifier according to claim 1 wherein the polysaccharide carbohydrate is tapioca, waxy corn starch or a mixture thereof.

5. The sensory modifier according to claim 1 wherein in anhydrous solvent comprises dipropylene glycol, polyethylene glycol, diglycerine or a mixture thereof.

6. The sensory modifier according to claim 1 wherein the sensory modifier further comprises a taurate copolymer.

7. A topical composition comprising:
a) sensory modifier comprising at least about 75% by weight amylopectin wherein the polysaccharide carbohydrate has been treated and swollen with a substantially anhydrous solvent and further wherein the polysaccharide carbohydrate and anhydrous solvent are at a weight ratio from about 1:4 to about 4:1 and heated from about 55 to about 90° C. for about 0.5 to about 6 hours after being combined and the sensory modifier with treated and swollen polysaccharide carbohydrate is free of gelation and further wherein the polysaccharide carbohydrate is functionally modified with a $C_{10}$-$C_{16}$ alkyl and/or alkenyl, and from about 0.01 to about 6 percent by weight of the polysaccharide is functionalized; and
b) a cosmetically acceptable carrier.

8. The topical composition according to claim 7 wherein the topical composition lightens skin, moisturizes skin and/or provides anti-aging benefits to skin.

9. The topical composition according to claim 7 wherein the anhydrous solvent comprises dipropylene glycol, polyethylene glycol, diglycerine or a mixture thereof.

10. The topical composition according to claim 7 wherein the anhydrous solvent has a polar component from about 7 to about 15, a hydrogen bonding component from about 14 to about 20, and a dispersion component form about 12 to about 19.

11. The topical composition according to claim 7 wherein the polysaccharide carbohydrate comprises from about 78 to about 100% by weight amylopectin, has an average initial particle diameter from about 1 to about 15 microns and an average swollen particle diameter that is from 1.5 to about 6 times greater than the initial particle diameter.

12. The topical composition according to claim 7 wherein the sensory modifier further comprises a taurate copolymer.

13. The topical composition according to claim 7 wherein the anhydrous solvent comprises from about 30 to about 50% by weight dipropylene glycol.

14. The topical composition according to claim 7 wherein the anhydrous solvent comprises polyethylene glycol and diglycene at a weight ratio from about 30:70 to about 70:30.

15. The topical composition according to claim 7 wherein the topical composition is substantially free of silicone elastomer.

16. The topical composition according to claim 7 wherein the composition further comprises avobenzophenone, octyl methoxycinnamae, alpha-hydroxy acid, zinc salt, conjugated linoleic acid, petroselinic acid, resorcinol, retinoid, niacinamide or a mixture thereof.

* * * * *